(12) United States Patent
Wu et al.

(10) Patent No.: US 11,690,552 B2
(45) Date of Patent: *Jul. 4, 2023

(54) CATHETER WITH STACKED SPINE ELECTRODE ASSEMBLY

(71) Applicant: BIOSENSE WEBSTER (ISRAEL) LTD., Yokneam (IL)

(72) Inventors: Steven Wu, San Jose, CA (US); Sungwoo Min, Fullerton, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 89 days.

This patent is subject to a terminal disclaimer.

(21) Appl. No.: 17/344,765

(22) Filed: Jun. 10, 2021

(65) Prior Publication Data

US 2021/0298656 A1 Sep. 30, 2021

Related U.S. Application Data

(63) Continuation of application No. 16/684,220, filed on Nov. 14, 2019, now Pat. No. 11,039,772, which is a
(Continued)

(51) Int. Cl.
*A61B 5/00* (2006.01)
*A61B 18/14* (2006.01)
(Continued)

(52) U.S. Cl.
CPC ............ *A61B 5/287* (2021.01); *A61B 5/6852* (2013.01); *A61B 5/6859* (2013.01); *A61B 18/00* (2013.01);
(Continued)

(58) Field of Classification Search
CPC ..... A61B 5/287; A61B 5/6852; A61B 5/6859; A61B 18/00; A61B 18/1492;
(Continued)

(56) References Cited

U.S. PATENT DOCUMENTS

| | | |
|---|---|---|
| 4,522,212 A | 6/1985 | Gelinas et al. |
| 4,529,912 A | 7/1985 | Northrup et al. |

(Continued)

FOREIGN PATENT DOCUMENTS

| | | |
|---|---|---|
| AU | 2015202258 A1 | 5/2015 |
| AU | 2016204351 A1 | 1/2017 |

(Continued)

OTHER PUBLICATIONS

Zhang Chuwei et al., "Fixation of Internal Jugular Vein Catheter to ECG Electrode with Sutures for Hemodialysis," Journal of Nursing Science, Sep. 2012, vol. 27 (17), 9 pages.
(Continued)

*Primary Examiner* — Adam Z Minchella
(74) *Attorney, Agent, or Firm* — Etan S. Chatlynne; Calderon Safran & Cole P.C.

(57) ABSTRACT

A catheter comprising an elongated catheter body, an electrode array distal of the catheter body, the array having a mounting member and at least first and second spine supports. Each spine support includes a base having a planar configuration, and a plurality of spines extending from the base, wherein the first base extends in a first plane and the second base extends in a second plane different from the first plane in the mounting member.

11 Claims, 10 Drawing Sheets

Related U.S. Application Data continuation of application No. 15/960,163, filed on Apr. 23, 2018, now Pat. No. 10,506,938, which is a continuation of application No. 14/754,566, filed on Jun. 29, 2015, now Pat. No. 9,949,656.

(51) Int. Cl.
*A61B 5/287* (2021.01)
*A61B 18/00* (2006.01)

(52) U.S. Cl.
CPC .. *A61B 18/1492* (2013.01); *A61B 2018/0016* (2013.01); *A61B 2018/00267* (2013.01); *A61B 2018/00577* (2013.01)

(58) Field of Classification Search
CPC .. A61B 2018/0016; A61B 2018/00267; A61B 2018/0057
See application file for complete search history.

(56) References Cited

U.S. PATENT DOCUMENTS

| | | |
|---|---|---|
| 5,702,438 A | 12/1997 | Avitall |
| 5,964,757 A | 10/1999 | Ponzi |
| 6,029,091 A | 2/2000 | de la Rama et al. |
| 6,071,279 A | 6/2000 | Whayne et al. |
| 6,071,280 A | 6/2000 | Edwards et al. |
| 6,071,282 A | 6/2000 | Fleischman |
| 6,123,699 A | 9/2000 | Webster, Jr. |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,210,407 B1 | 4/2001 | Webster |
| 6,267,746 B1 | 7/2001 | Bumbalough |
| 6,415,187 B1 | 7/2002 | Kuzma et al. |
| 6,522,932 B1 | 2/2003 | Kuzma et al. |
| 6,652,515 B1 | 11/2003 | Maguire et al. |
| 6,658,302 B1 | 12/2003 | Kuzma et al. |
| 6,961,602 B2 | 11/2005 | Fuimaono et al. |
| 7,027,851 B2 | 4/2006 | Mejia |
| 7,089,045 B2 | 8/2006 | Fuimaono et al. |
| 7,099,712 B2 | 8/2006 | Fuimaono et al. |
| 7,228,164 B2 | 6/2007 | Fuimaono et al. |
| 7,257,435 B2 | 8/2007 | Plaza |
| 7,412,274 B2 | 8/2008 | Mejia |
| 7,429,261 B2 | 9/2008 | Kunis et al. |
| 7,561,907 B2 | 7/2009 | Fuimaono et al. |
| 8,187,267 B2 | 5/2012 | Pappone et al. |
| 8,206,404 B2 | 6/2012 | De La Rama et al. |
| 8,271,099 B1 | 9/2012 | Swanson |
| 8,391,947 B2 | 3/2013 | Urman et al. |
| 8,486,063 B2 | 7/2013 | Werneth et al. |
| 8,565,894 B2 | 10/2013 | Vetter et al. |
| 8,603,069 B2 | 12/2013 | Selkee |
| 8,734,440 B2 | 5/2014 | Wu |
| 8,744,599 B2 | 6/2014 | Tegg |
| 8,974,454 B2 | 3/2015 | De La Rama et al. |
| 8,979,837 B2 | 3/2015 | De La Rama et al. |
| 9,044,245 B2 | 6/2015 | Condie et al. |
| 9,392,971 B2 | 7/2016 | Asirvatham et al. |
| 9,820,664 B2 | 11/2017 | Hoitink et al. |
| 9,833,608 B2 | 12/2017 | Masson |
| 9,907,480 B2 | 3/2018 | Basu et al. |
| 10,220,187 B2 | 3/2019 | De La Rama et al. |
| 10,576,244 B2 | 3/2020 | De La Rama et al. |
| 10,595,740 B2 | 3/2020 | Hoitink et al. |
| 2003/0130572 A1 | 7/2003 | Phan et al. |
| 2005/0159741 A1 | 7/2005 | Paul et al. |
| 2006/0074412 A1 | 4/2006 | Zerfas et al. |
| 2009/0198300 A1 | 8/2009 | Zhang et al. |
| 2009/0240248 A1 | 9/2009 | Deford et al. |
| 2010/0087848 A1 | 4/2010 | Kim et al. |
| 2010/0286684 A1 | 11/2010 | Hata et al. |
| 2011/0106075 A1 | 5/2011 | Jimenez |
| 2011/0118726 A1 | 5/2011 | De La Rama et al. |
| 2012/0010490 A1 | 1/2012 | Kauphusman et al. |
| 2012/0271302 A1 | 10/2012 | Behl et al. |
| 2012/0296232 A1 | 11/2012 | Ng |
| 2013/0053841 A1 | 2/2013 | Grunewald |
| 2013/0172715 A1 | 7/2013 | Just et al. |
| 2013/0253504 A1 | 9/2013 | Fang |
| 2013/0274582 A1 | 10/2013 | Afonso et al. |
| 2014/0200639 A1 | 7/2014 | De La Rama |
| 2014/0296902 A1 | 10/2014 | Huszar et al. |
| 2014/0316496 A1 | 10/2014 | Masson et al. |
| 2014/0350564 A1 | 11/2014 | Huszar et al. |
| 2015/0105645 A1 | 4/2015 | Subramaniam et al. |
| 2015/0112329 A1 | 4/2015 | Ng |
| 2015/0141785 A1 | 5/2015 | Hayam et al. |
| 2015/0351652 A1 | 12/2015 | Marecki et al. |
| 2015/0374252 A1 | 12/2015 | De La Rama et al. |
| 2016/0143588 A1* | 5/2016 | Hoitink ............... A61B 5/6859 600/374 |
| 2016/0213916 A1* | 7/2016 | De La Rama ....... A61B 5/6859 |
| 2016/0317094 A1 | 11/2016 | Byrd et al. |
| 2016/0331471 A1* | 11/2016 | Deno .................. A61B 34/20 |
| 2016/0374582 A1 | 12/2016 | Wu et al. |
| 2016/0374753 A1 | 12/2016 | Wu et al. |
| 2017/0000365 A1 | 1/2017 | Wu et al. |
| 2017/0042449 A1 | 2/2017 | Deno et al. |
| 2017/0049348 A1 | 2/2017 | Deno et al. |
| 2017/0112404 A1 | 4/2017 | De La Rama et al. |
| 2017/0112405 A1 | 4/2017 | Sterrett et al. |
| 2017/0319269 A1 | 11/2017 | Oliverius et al. |
| 2017/0367756 A1 | 12/2017 | Sliwa et al. |
| 2018/0050190 A1 | 2/2018 | Masson |
| 2018/0070845 A1 | 3/2018 | Hoitink et al. |
| 2018/0116539 A1 | 5/2018 | Olson et al. |

FOREIGN PATENT DOCUMENTS

| | | |
|---|---|---|
| AU | 2016204353 A1 | 1/2017 |
| AU | 2016204355 A1 | 1/2017 |
| CA | 2934209 A1 | 12/2016 |
| CA | 2934211 A1 | 12/2016 |
| CA | 2934214 A1 | 12/2016 |
| CN | 1323180 A | 11/2001 |
| CN | 101304778 A | 11/2008 |
| CN | 101687093 A | 3/2010 |
| CN | 101797181 A | 8/2010 |
| CN | 101856271 A | 10/2010 |
| CN | 102292044 A | 12/2011 |
| CN | 102448358 A | 5/2012 |
| CN | 102551704 A | 7/2012 |
| CN | 102639077 A | 8/2012 |
| CN | 102711645 A | 10/2012 |
| CN | 102846374 A | 1/2013 |
| CN | 102895028 A | 1/2013 |
| CN | 102961183 A | 3/2013 |
| CN | 103027677 A | 4/2013 |
| CN | 103281978 A | 9/2013 |
| CN | 103547213 A | 1/2014 |
| CN | 103889348 A | 6/2014 |
| CN | 103908336 A | 7/2014 |
| CN | 203693745 U | 7/2014 |
| CN | 104010585 A | 8/2014 |
| CN | 101797181 B | 12/2015 |
| CN | 102961183 B | 8/2016 |
| CN | 105960201 A | 9/2016 |
| CN | 106264715 A | 1/2017 |
| CN | 106264716 A | 1/2017 |
| CN | 106308790 A | 1/2017 |
| CN | 103315806 B | 6/2017 |
| CN | 103417290 B | 8/2018 |
| EP | 0856291 A2 | 8/1998 |
| EP | 0779059 B1 | 4/2004 |
| EP | 2664295 A1 | 11/2013 |
| EP | 2732843 A1 | 5/2014 |
| EP | 2752153 A1 | 7/2014 |
| EP | 2907462 A1 | 8/2015 |
| EP | 3023052 A1 | 5/2016 |
| EP | 3111871 A1 | 1/2017 |

(56) References Cited

FOREIGN PATENT DOCUMENTS

| | | | |
|---|---|---|---|
| EP | 3111872 A1 | 1/2017 | |
| EP | 3114987 A1 | 1/2017 | |
| IN | 201614021431 A | 12/2016 | |
| IN | 201614021432 A | 12/2016 | |
| IN | 201614021450 A | 12/2016 | |
| JP | 2003510160 A | 3/2003 | |
| JP | 2003290247 A | 10/2003 | |
| JP | 2011147802 A | 8/2011 | |
| JP | 2011172785 A | 9/2011 | |
| JP | 2012130392 A | 7/2012 | |
| JP | 2013192948 A | 9/2013 | |
| JP | 2014004368 A | 1/2014 | |
| JP | 2014506171 A | 3/2014 | |
| JP | 2015100706 A | 6/2015 | |
| JP | 2015112484 A | 6/2015 | |
| JP | 2016104129 A | 6/2016 | |
| JP | 2017012750 A | 1/2017 | |
| JP | 2017012755 A | 1/2017 | |
| JP | 2017038919 A | 2/2017 | |
| RU | 2016125763 A | 1/2018 | |
| WO | 2004015761 A1 | 2/2004 | |
| WO | 2013028998 A2 | 2/2013 | |
| WO | 2014022436 A1 | 2/2014 | |
| WO | 2014113612 A1 | 7/2014 | |
| WO | 2014168987 A1 | 10/2014 | |
| WO | 2014172398 A1 | 10/2014 | |
| WO | 2015044086 A1 | 4/2015 | |
| WO | 2015057521 A1 | 4/2015 | |
| WO | 2015095577 A1 | 6/2015 | |
| WO | 2015130824 A1 | 9/2015 | |
| WO | 2016001015 A1 | 1/2016 | |

OTHER PUBLICATIONS

European Examination Report in corresponding European Application No. 15195293.4, dated Jan. 19, 2017, 6 pages.
Extended European Search Report for European Application No. 15195293.4, dated Apr. 12, 2016, 5 pages.
Extended European Search Report for Application No. 19164969.8 dated Jul. 19, 2019, 11 pages.
Extended European Search Report for European Application No. 16176559.9, dated Nov. 7, 2016, 6 pages.
Extended European Search Report for European Application No. 16176598.7, dated Nov. 7, 2016, 4 pages.
Extended European Search Report for European Application No. 16176803.1, dated Dec. 12, 2016, 5 pages.
Extended European Search Report for European Application No. 18166678.5 , dated Jun. 28, 2018, 8 pages.
Israeli Patent Application No. 246414, filed on Jun. 23, 2016, 2 pages (English Abstract attached—also corresponds to U.S. Pat. No. 20160374753).
Sraeli Patent Application No. 246415, filed on Jun. 23, 2016, 2 pages (English Abstract attached—also corresponds to U.S. Pat. No. 20160374582).
Israeli Patent Application No. 246416, filed on Jun. 23, 2016, 2 pages (English Abstract attached—also corresponds to U.S. Pat. No. 20170000365).
Office Action for European Application No. 15195293.4, dated Jul. 20, 2017, 5 pages.
Michael A. Speidel et al., "Three-dimensional Tracking of Cardiac Catheters using an Inverse Geometry x-ray Fluoroscopy System," Medical Physics, Dec. 2010, vol. 37 (12), pp. 6377-6389.
Extended European Search Report for European Application No. EP22195201.3, dated Jan. 17, 2023, 09 pages.

\* cited by examiner

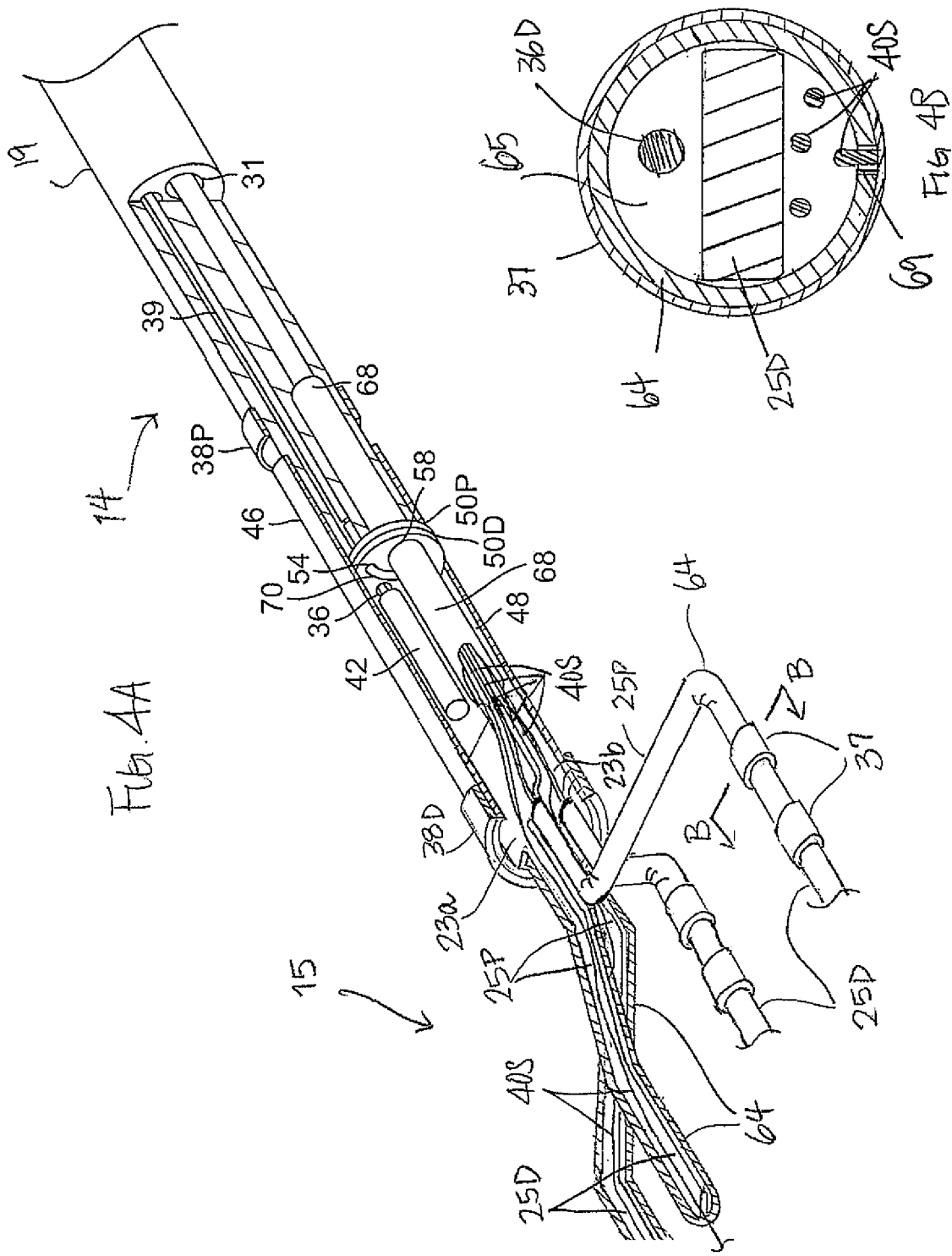

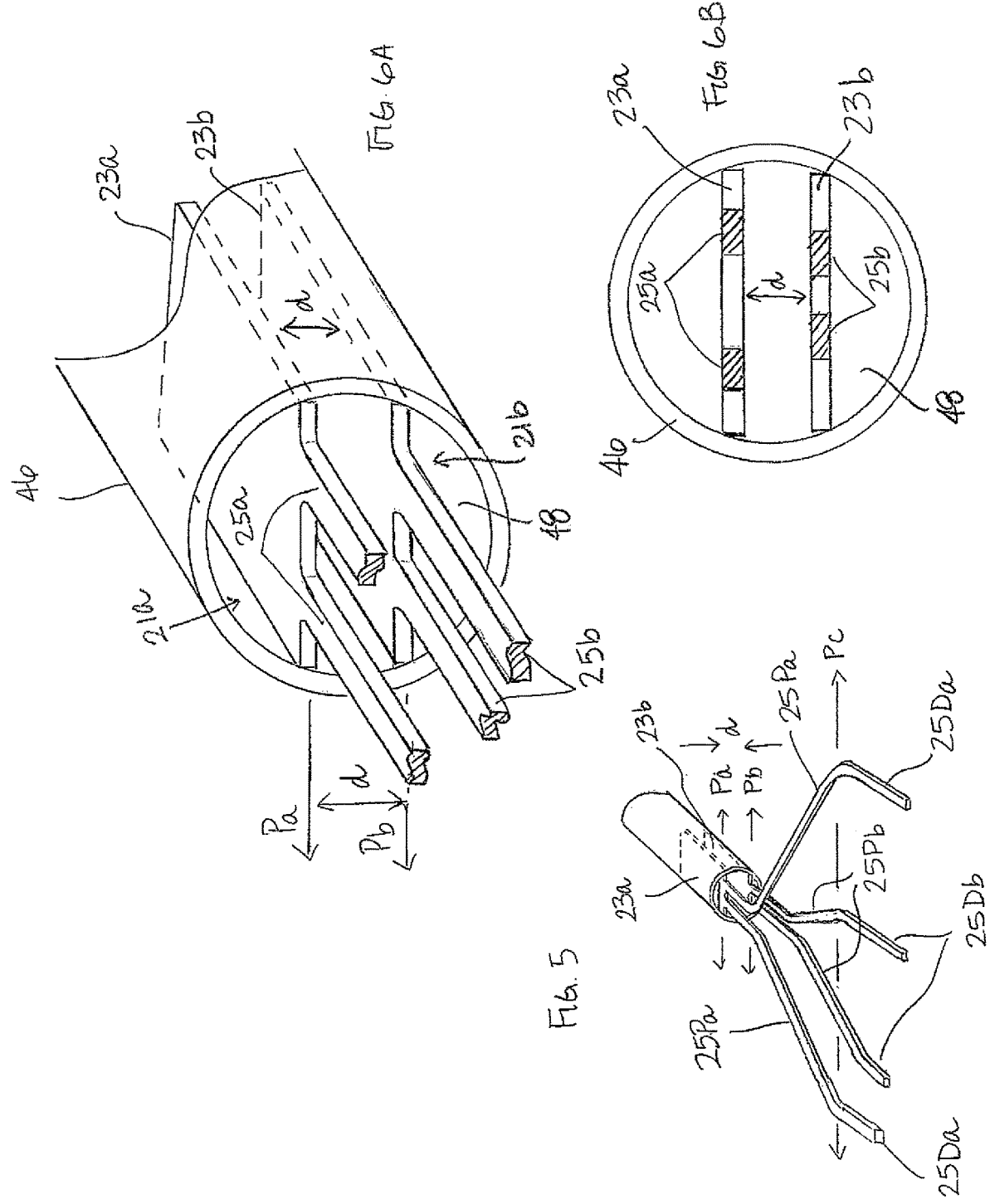

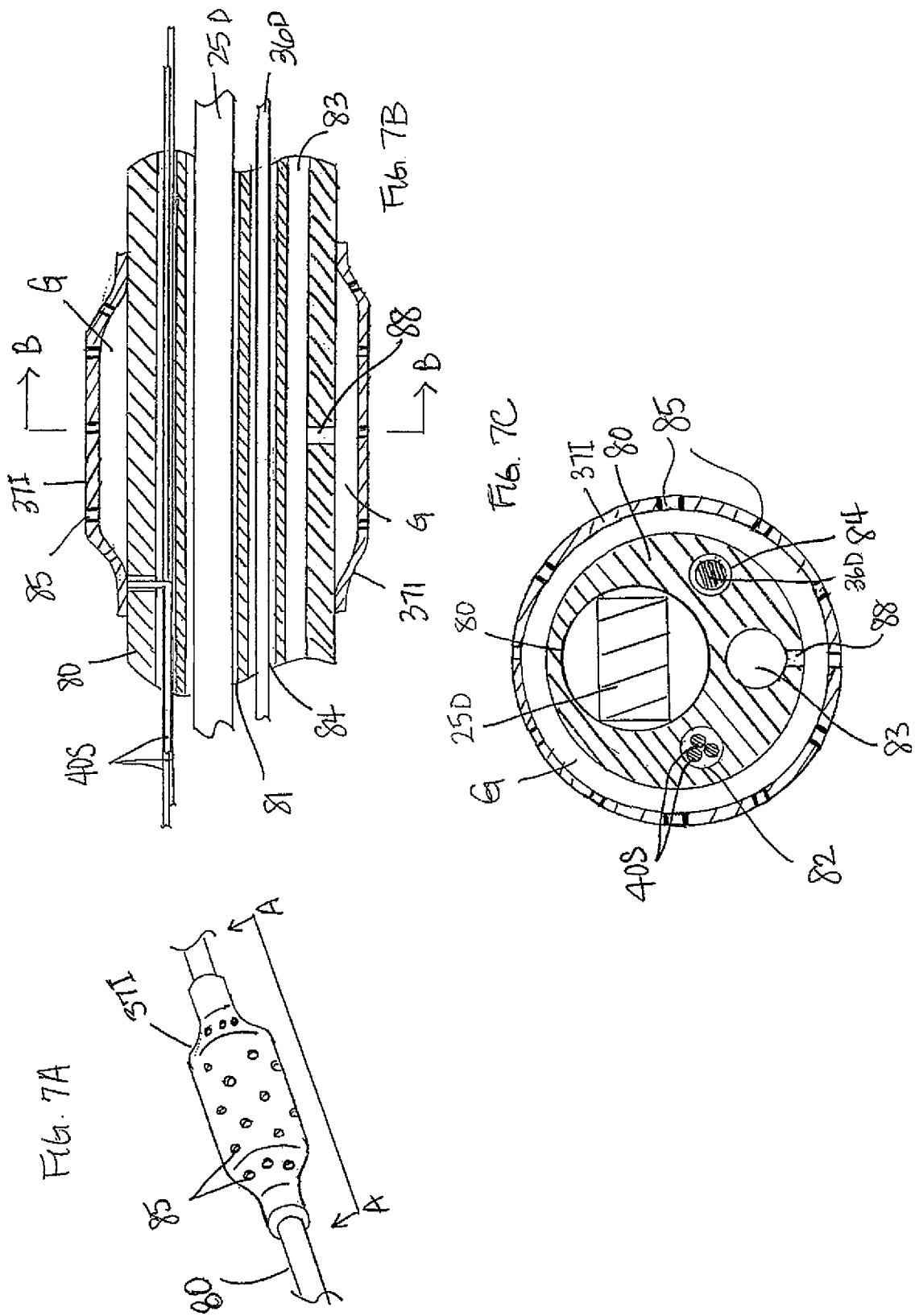

CATHETER WITH STACKED SPINE ELECTRODE ASSEMBLY

CROSS REFERENCE TO RELATED APPLICATION

The present application is a Continuation under 35 U.S.C. § 120 of U.S. patent application Ser. No. 16/684,220, filed Nov. 14, 2019, which is a Continuation under 35 U.S.C. § 120 of U.S. patent application Ser. No. 15/960,163, filed Apr. 23, 2018, now U.S. Pat. No. 10,506,938 which is a Continuation under 35 U.S.C. § 120 of U.S. patent application Ser. No. 14/754,566, filed Jun. 29, 2015, now U.S. Pat. No. 9,949,656. The entire contents of these applications are incorporated by reference herein in their entirety.

FIELD OF INVENTION

This invention relates to catheters, in particular, intravascular catheters for tissue diagnostics and ablation.

BACKGROUND

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in the tissue region, for example, one of the atria or one of the ventricles. Regardless of the sources, unwanted signals are conducted elsewhere through heart tissue where they can initiate or continue arrhythmia.

Procedures for treating arrhythmia include surgically disrupting the origin of the signals causing the arrhythmia, as well as disrupting the conducting pathway for such signals. More recently, it has been found that by mapping the electrical properties of the endocardium and the heart volume, and selectively ablating cardiac tissue by application of energy, it is possible to cease or modify the propagation of unwanted electrical signals from one portion of the heart to another. The ablation process destroys the unwanted electrical pathways by formation of non-conducting lesions.

In this two-step procedure-mapping followed by ablation-electrical activity at points in the heart is typically sensed and measured by advancing a catheter containing one or more electrical sensors into the heart, and acquiring data at a multiplicity of points. These data are then utilized to select the target areas at which ablation is to be performed.

For greater mapping resolution, it is desirable for a mapping catheter to provide very high density signal maps through the use of a multitude of electrodes sensing electrical activity within a small area, for example, about a square centimeter. For mapping within an atria or a ventricle (for example, an apex of a ventricle), it is desirable for a catheter to collect larger amounts of data signals within shorter time spans. It is also desirable for such a catheter to be adaptable to different tissue surfaces, for example, flat, curved, irregular or nonplanar surface tissue, yet remain in a predetermined configuration where electrode spatial relationships are generally maintained during sensing and mapping. Moreover, with the need for greater electrode density, it is desirable for the catheter to accommodate additional electrode support structures in a manner that allows for more complex electrode arrays with improved tissue contact and manufacturability.

SUMMARY OF THE INVENTION

The catheter of the present invention provides a distal electrode assembly or array that has a more simplistic construction for improved manufacturability and yet is able to accommodate complex electrode arrays for greater electrode density and tissue contact. The catheter includes an electrode array comprising a mounting member with a lumen and one or more spine supports, with each spine support including a base having a planar configuration, and a plurality of spines extending from the base, wherein each base occupies in a different plane in the lumen.

With a planar configuration, each base is advantageously positioned in the mounting member or stem in a "stacked" configuration where each base occupies a different plane in the lumen of the stem. For example, the "stacked" configuration may include a "storied" (or "multi-storied") configuration, where each occupies a different plane in the lumen of the mounting stem. Depending on the volume of space available in the stem and the plurality of bases, the bases may be aligned and be separated by a space gap from adjacent bases, similar to floors of a multi-storied building wherein each floor occupies a different plane and is separated by a space gap from adjacent floors.

In some embodiments, each spine includes a proximal portion and a distal portion, and the distal portions of the array extend in a common plane. The distal portions of the array may be linear. The distal portions may be parallel with each other. The common plane may be parallel with at least one of the planes occupied by the bases.

In some embodiments, each spine has a free distal end. In some embodiments, each spine has a distal end that is connected to at least one distal end of another spine.

The present invention is also directed to catheter comprising an elongated catheter body, and an electrode array, the array comprising a mounting stem and at least first and second spine supports, each spine support including a base having a planar configuration, and a plurality of spines extending from the base. The array also includes a nonconductive covering on each spine, and one or more electrodes carried on the spines. The first base is fixed in a lumen of the stem at a first plane and the second base is fixed in the lumen of the stem at a second plane different from the first plane.

The present invention is further directed to a catheter comprising an elongated catheter body, an electrode array distal of the catheter body, the array comprising a mounting stem, and at least first and second spine supports, each spine support including a base having a planar configuration, and a plurality of spines extending from the base. The array also includes a nonconductive covering on each spine, and one or more electrodes carried on the spines. The first base is fixed in a lumen of the stem at a first plane, the second base is fixed in the lumen of the stem at a second plane different from the first plane, and each spine has a distal linear portion, and the distal linear portions of the array are parallel with each other.

In some embodiments, the distal linear portions of the array are parallel with a longitudinal axis of the stem.

In some embodiments, the plurality of spines ranges between about two and six.

BRIEF DESCRIPTION OF THE DRAWINGS

These and other features and advantages of the present invention will be better understood by reference to the following detailed description when considered in conjunction with the accompanying drawings wherein:

FIG. 4A is a perspective view of a junction between the deflection section and the distal electrode assembly, with parts broken away, in accordance with one embodiment.

FIG. 4B is an end cross-sectional view of a ring electrode mounted on a spine of FIG. 4A, taken along line B-B.

FIG. 5 is a partial perspective view of a spine support and a mounting stem, of FIG. 4A.

FIG. 6A is a detailed perspective view of the spine support and mounting stem of FIG. 5.

FIG. 6B is an end view of the spine support and mounting stem of 6A.

FIG. 7A is a perspective view of an irrigated ring electrode mounted on a spine, in accordance with one embodiment.

FIG. 7B is a side cross-sectional view of the irrigated ring electrode of FIG. 7A, taken along line A-A.

FIG. 7C is an end cross-sectional view of the irrigated ring electrode of FIG. 7B, taken along line B-B.

DETAILED DESCRIPTION OF THE INVENTION

Figure 1:
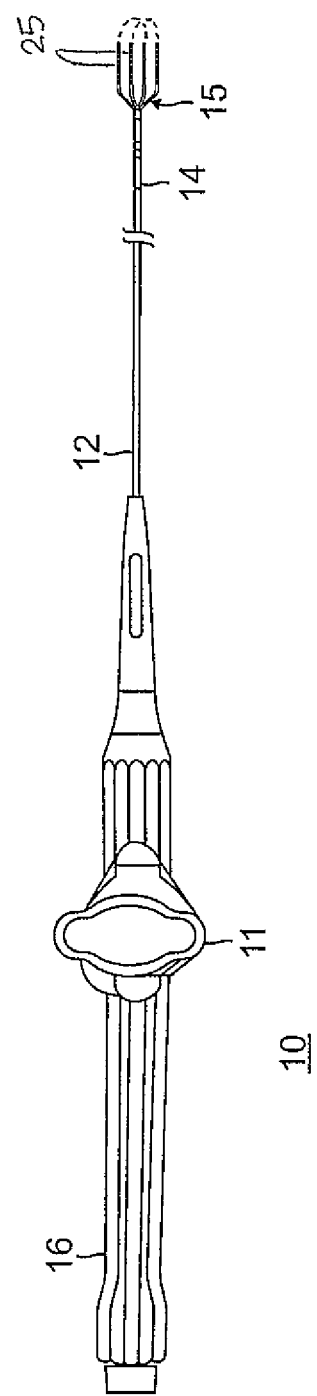
FIG. 1 is a perspective view of a catheter of the present invention, in accordance with some embodiments.

As shown in FIG. 1, the catheter 10 comprises an elongated catheter body 12, an intermediate deflection section 14, a distal electrode assembly or array 15 with a plurality of spines, and a deflection control handle 16 attached to the proximal end of the catheter body 12. In accordance with a feature of the present invention, the distal electrode array 15 includes multiple spine supports that enable the spines to be mounted to the distal end of the catheter in a spatially efficient manner that accommodates more complex spine geometries while improving electrode-to-tissue contact and manufacturability of the catheter.

Figure 2A:
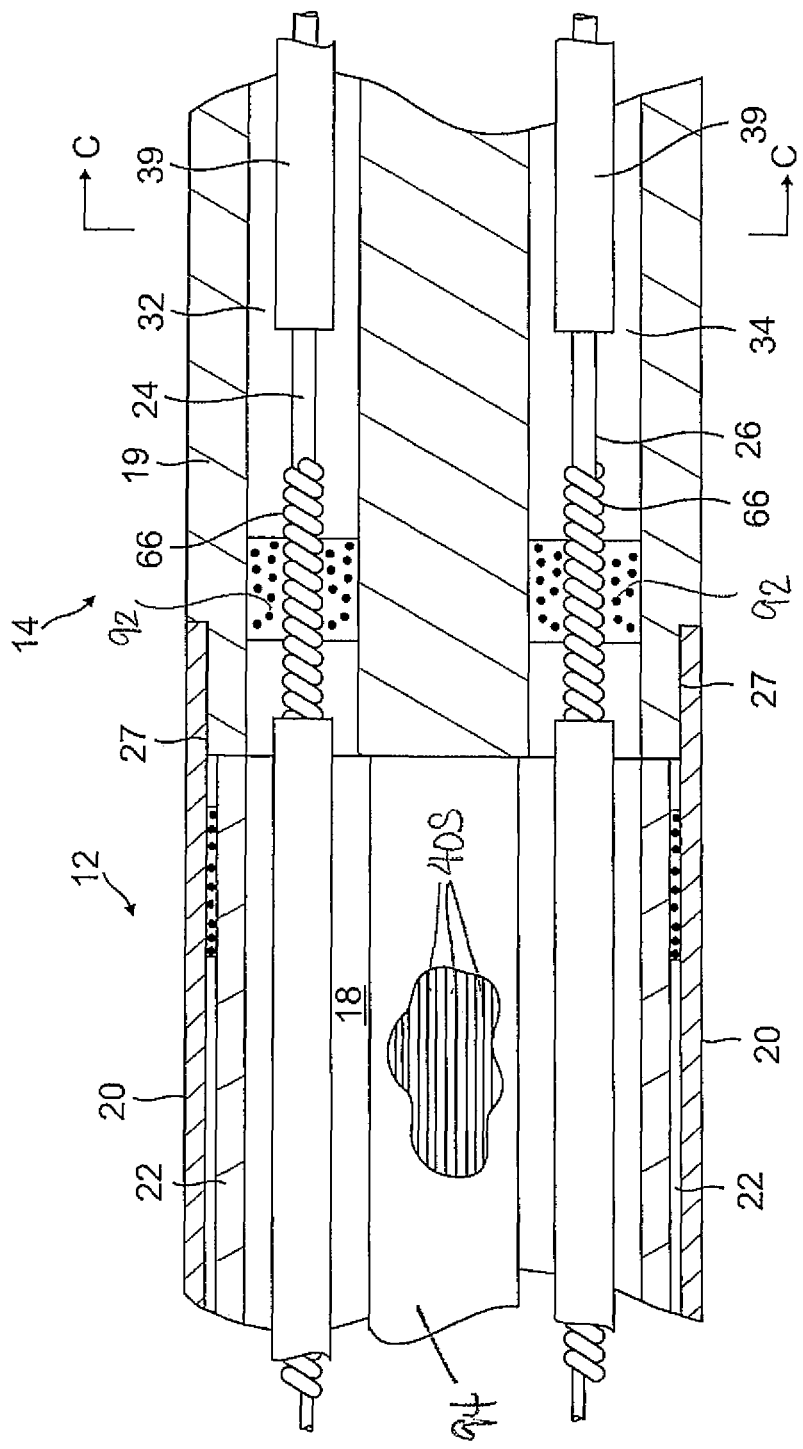
FIG. 2A is a side cross-sectional view of the catheter of FIG. 1, including a junction between a catheter body and a deflection section, taken along a first diameter.
Figure 2B:
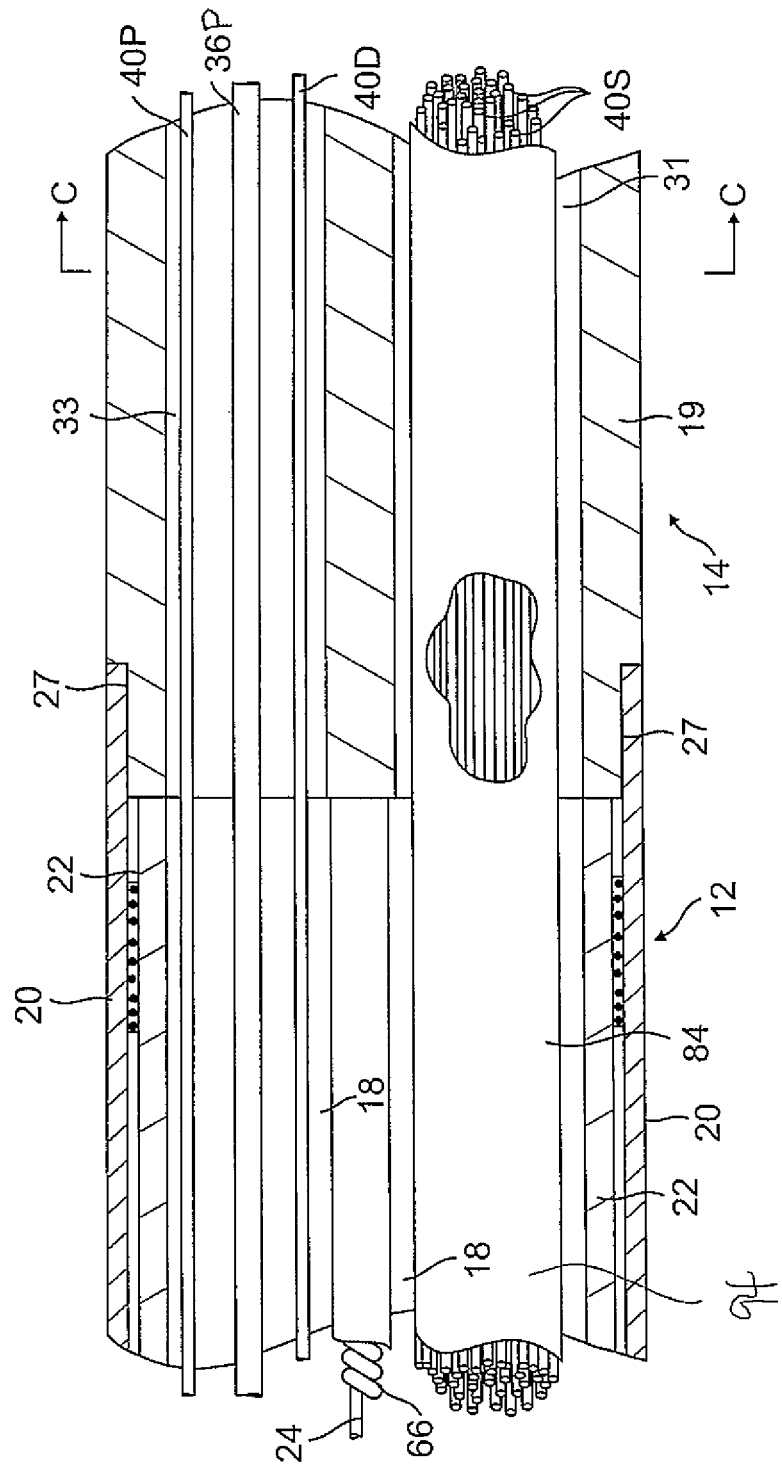
FIG. 2B is a side cross-sectional view of the catheter of FIG. 1, including the junction of FIG. 2A, taken along a second diameter generally perpendicular to the first diameter.

With reference to FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. In some embodiments, the catheter body 12 comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 rotates in a corresponding manner.

The outer diameter of the catheter body 12 is not critical. Likewise, the thickness of the outer wall 20 is not critical, but is thin enough so that the central lumen 18 can accommodate a puller wire, one or more lead wires, and any other desired wires, cables or tubes. If desired, the inner surface of the outer wall 20 is lined with a stiffening tube 22 to provide improved torsional stability.

Figure 2C:
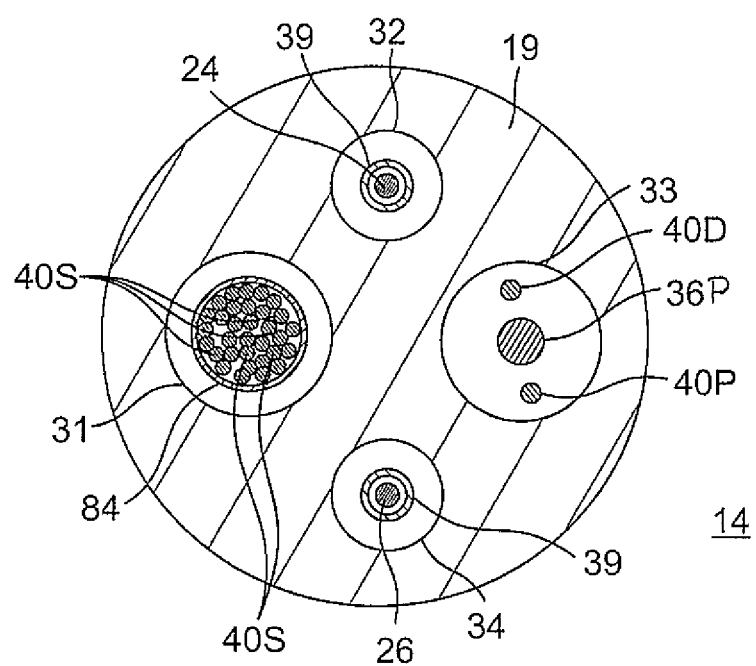
FIG. 2C is an end cross-sectional view of the deflection section of FIGS. 2A and 2B, taken along line C-C.

As shown in FIGS. 2A, 2B and 2C, the intermediate section 14 comprises a shorter section of tubing 19 having multiple lumens, for example, four off-axis lumens 31, 32, 33 and 34. The first lumen 31 carries a plurality of lead wires 40S for ring electrodes 37 mounted on the array 15. The second lumen 32 carries a first puller wire 24. The third lumen 33 carries a cable 36 for an electromagnetic position sensor 42 and a plurality of lead wires 40D and 40P for distal and proximal ring electrodes 38D and 38P carried on the catheter proximally of the distal electrode array 15. The fourth lumen 34 (for example, diametrically opposite of the second lumen 32 in the illustrated embodiment) carries a second puller wire 26. The tubing 19 is made of a suitable non-toxic material that is preferably more flexible than the catheter body 12. One suitable material for the tubing 19 is braided polyurethane, i.e., polyurethane with an embedded mesh of braided stainless steel or the like. The size of each lumen is not critical, but is sufficient to house the lead wires, puller wires, the cable and any other components.

The useful length of the catheter, i.e., that portion that can be inserted into the body excluding the distal electrode array 15, can vary as desired. Preferably the useful length ranges from about 110 cm to about 120 cm. The length of the intermediate section 14 is a relatively smaller portion of the useful length, and preferably ranges from about 3.5 cm to about 10 cm, more preferably from about 5 cm to about 6.5 cm.

A means for attaching the catheter body 12 to the intermediate section 14 is illustrated in FIGS. 2A and 2B. The proximal end of the intermediate section 14 comprises an outer circumferential notch 27 that receives the inner surface of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

Figure 3A:
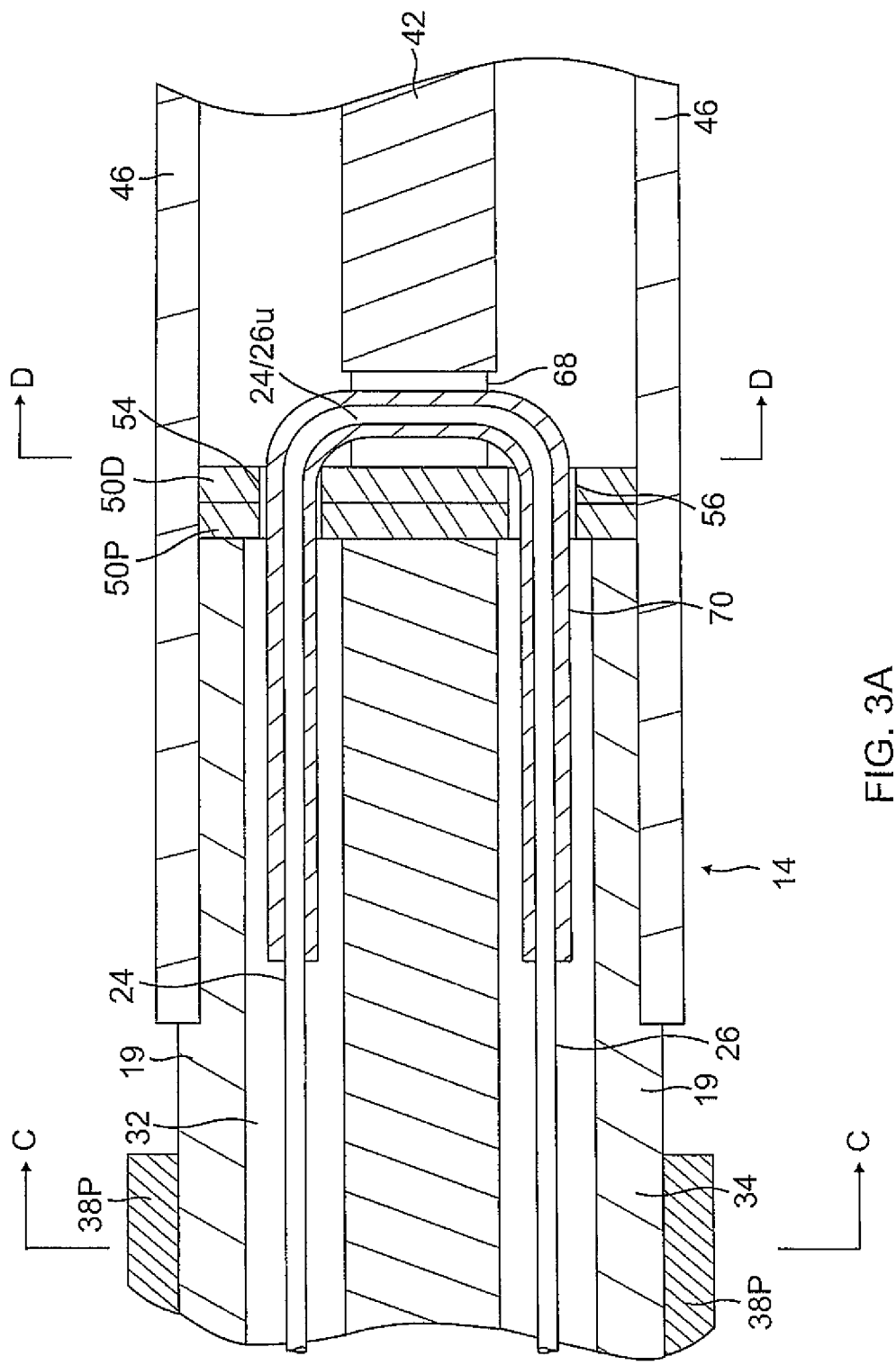
FIG. 3A is a side cross-sectional view of the catheter of FIG. 1, including a junction between the deflection section and a distal electrode assembly, taken along a first diameter.
Figure 3B:
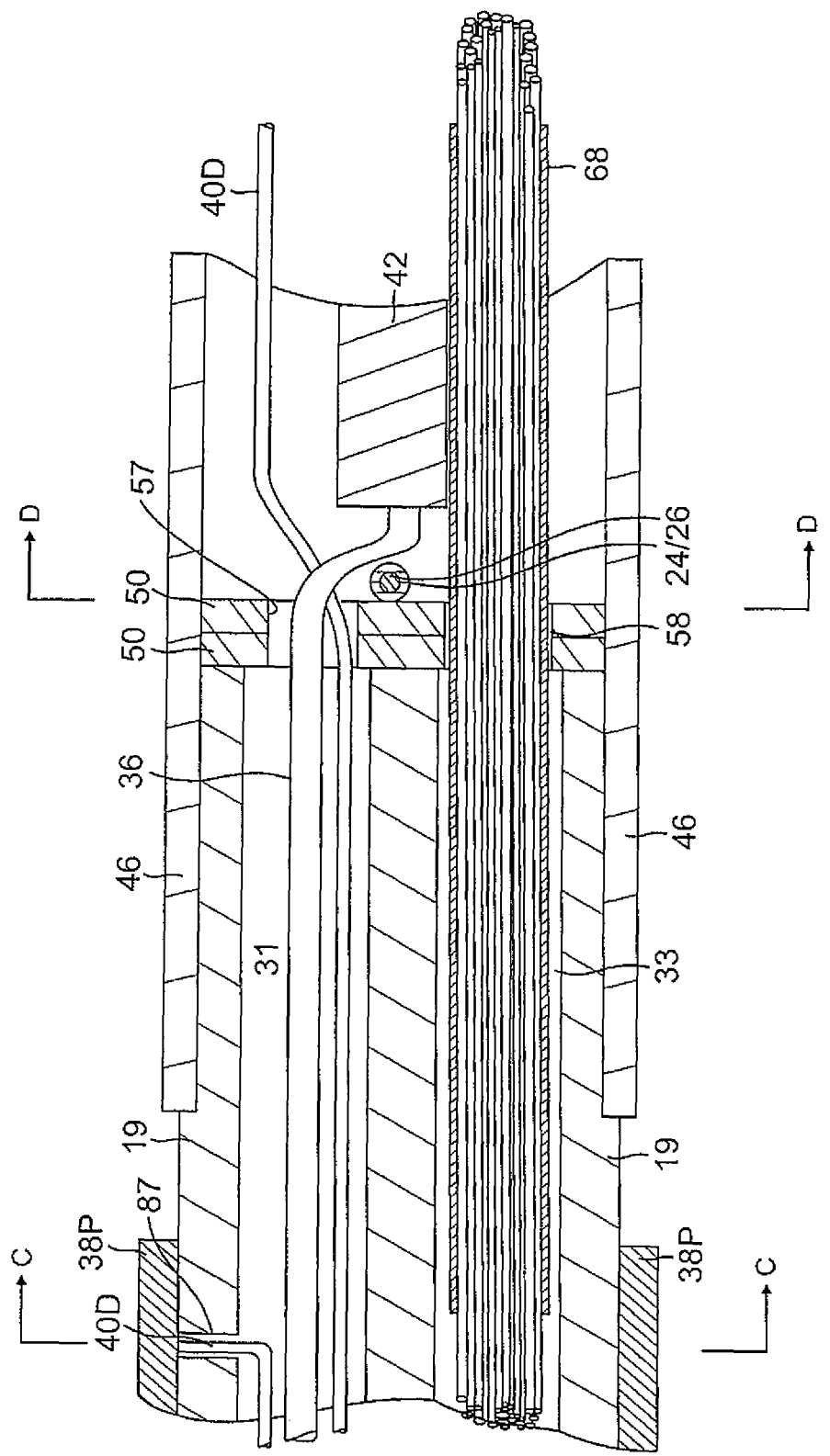
FIG. 3B is a side cross-sectional view of the junction of FIG. 3A, taken along a second diameter generally perpendicular to the first diameter.

As shown in FIGS. 3A and 3B, the distal electrode array 15 includes a mounting member or stem 46 in the form of a short tubing mounted on a distal end of the tubing 19 of the intermediate deflection section 14. It is understood that the stem may be mounted onto the distal end of the catheter body 12 where the catheter includes no deflection section. The stem 46 has a central lumen 48 to house various components. The intermediate section 14 and stem 46 are attached by glue or the like. The stem 46 may be constructed of any suitable material, including nitinol.

Figure 3C:
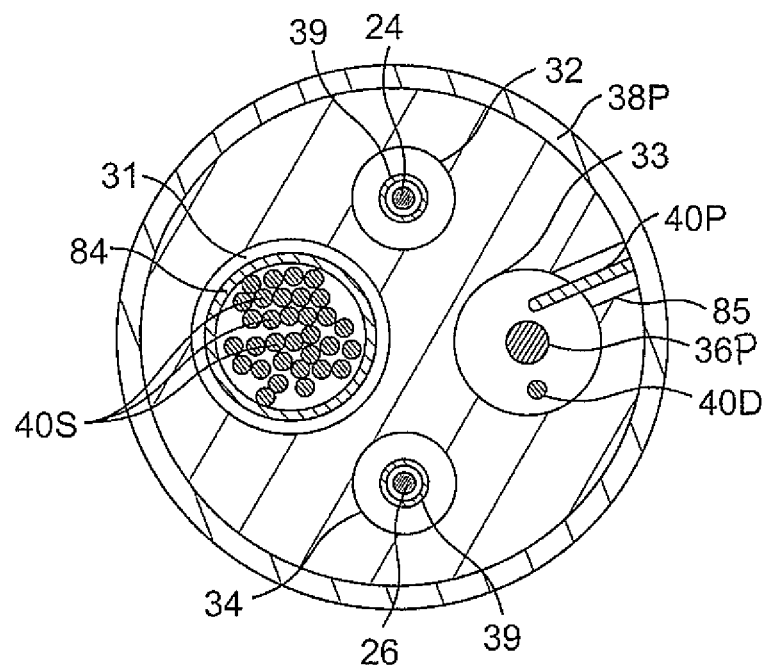
FIG. 3C is an end cross-sectional view of the deflection section of FIGS. 3A and 3B, taken along line C-C.
Figure 3D:
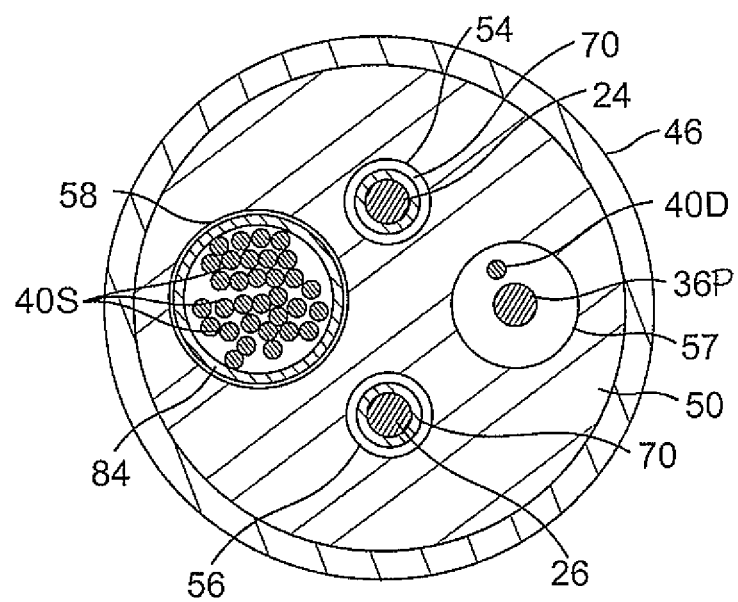
FIG. 3D is an end cross-sectional view of the junction of FIGS. 3A and 3B, taken along line D-D.

As shown in FIG. 4A, the stem 46 houses various components, including, for example, the electromagnetic position sensor 42, and a distal anchor for the puller wires 24 and 26. In the disclosed embodiment, the distal anchor includes one or more washers, for example, a distal washer 50D and a proximal washer 50P, each of which has a plurality of matching axial through-holes that allow passage of components between the deflection section 14 and the stem 46 while maintaining axial alignment of these components relative to the longitudinal axis 95 of the catheter 10. As shown in FIG. 3D, the through-holes include holes 54 and 56 that are axially aligned with the second and fourth lumens 32 and 34 of the tubing 19, respectively, to receive a distal end of puller wires 24 and 26, respectively. It is understood that the puller wires 24 and 26 may actually form a single tensile member with a distal U-bend section that passes through the holes 54 and 56. With tension on the washers 50D and 50P exerted by the U-bend section of the puller wires 24 and 26, the washers firmly and fixedly abut against the distal end of the tubing 19 of the deflection section 14 to distally anchor the U-bend section.

As shown in FIG. 3D, each washer also includes through-hole 58 which is axially aligned with the first lumen 31 and allows passage of the lead wires 40S from the deflection section 14 and into the lumen 48 of the stem 46. Each washer further includes through-hole 57 which is axially aligned with the third lumen 33 and allows passage of the sensor cable 36 from the deflection section 14 into lumen 48 of the stem 46 where the electromagnetic position sensor 42 is housed. The lead wire 40D also passes through the hole 57 to enter the lumen 48 for attachment to the distal ring electrode 38D carried on the outer surface of the stem 46 via an opening (not shown) formed in the side wall of the stem 46 through which a distal end of the lead wire 40D is welded or otherwise attached to the distal ring electrode 38D, as known in the art. Carried on the outer surface of the tubing 19 near the distal end of the intermediate deflection section 14, a proximal ring electrode 38P is connected to lead wire 40P via an opening 87 (FIG. 3B) formed in the side wall of the tubing 19 that provides communication between the third lumen 33 and outside of the tubing 19. The distal end of the lead wire is welded or otherwise attached to the proximal ring electrode 38P as known in the art.

With reference to FIGS. 4A, 5, 6A and 6B, multiple spine supports 21 are anchored in the lumen 48 near the distal end of the stem 46, with each support 21 having a base 23 and a plurality of spines 25 extending from a distal edge of the base 23. Each spine 25 has at least a proximal portion 25P and a distal portion 25D. The spines 25 may extend like fingers with free distal ends (see solid lines in FIG. 1), or the spines may have their distal ends connected forming closed loops (see broken lines in FIG. 1). With a planar configuration, each base 23 is advantageously positioned in the stem 46 in a "stacked" configuration where each base 23 occupies a different plane in the stem 46. For example, the "stacked" configuration may include a "storied" or "multi-storied" configuration, where each base 23 is aligned with each other, occupying a different plane in the stem 46. Depending on the volume of space available in the stem and the plurality of bases, the bases may be separated by a space gap from adjacent bases 23, similar to floors of a multi-storied building wherein each floor occupies a different plane and is separated by a space gap from adjacent floors. It is understood that the stem 46 may have any appropriate or desired cross-sectional shape, including, for example, circular, oval, rectangular and polygonal.

In the illustrated embodiment, the array 15 has a first spine support 21a and a second spine support 21b, where the bases 23a and 23b occupy or extend in planes Pa and Pb, respectively, and are separated by a distance d. As such, the spines 25a and 25b extending from the bases 23a and 23b have the freedom to extend in multiple different directions while the bases 23a and 23b occupy minimal space in the stem 46. Construction and manufacturability of the array 15 are also simplified by the stacking arrangement of the bases.

More complex array geometries may include the distal spine portions 25 Da and 25Db all extending within a common plane Pc, despite their respective bases 23a and 23b being in different planes Pa and Pb within the stem 46 (see FIG. 5). For example, the planes Pa and Pb may be parallel or nonparallel to each other, as desired or appropriate, and the plane Pc may be co-planar with the plane Pa or with the plane Pb, or it may define a different plane from planes Pa and Pb (parallel or nonparallel with plane Pc).

It is understood, especially from FIGS. 6A and 6B, that the stem 46 can accommodate additional bases in its lumen 48 between the bases 23a and 23b, above the base 23a and/or below the base 23b to provide the array 15 with additional spines, as desired or appropriate. The bases 23 securely anchor the spines 15 within the stem 46, and greatly simplify the assembly and mounting of the array 15 onto the distal end of the catheter, whether the stem is mounted on a distal end of the deflection section 14, or of the catheter body 12 where the catheter has no deflection section 14.

As best shown in FIG. 6B, the proximal spine portions 25 Pa may extend from its base 23a at different locations from the locations at which the proximal spine portions 25Pb may extend from its base 23b, so that the proximal spine portions 25 Pa are laterally offset from the proximal spine portions 25Pb, even though the bases 23a and 23b are aligned.

In the illustrated embodiments, both of the proximal spine portions 25P and the distal spine portions are linear 25D, however, the proximal spine portions 25P diverge from the longitudinal axis of the stem 46, whereas the distal spine portions 25D are parallel with the longitudinal axis of the stem 46.

Each spine 25 has a nonconductive tubing or covering 64 along its length, as shown in FIG. 4A. On each spine 25, one or more ring electrodes 37 are mounted over the covering 64. Proximal of the array 15, the lead wires 40S for the ring electrodes 37 extend through a protective polytube 68. The lead wires 40S diverge near the distal end of the polytube 68, and extend toward their respective spine 25, into lumen 65 of the respective nonconductive covering 64. As shown in FIG. 4B, each lead wire 40S is connected to its respective ring electrode 37 via a respective opening 69 formed in the side wall of the covering 64 through which a distal end of the lead wire reaches outside of the covering 64 and is welded or otherwise attached to its ring electrode 37.

In other embodiments, irrigated ring electrodes 371 are carried on the spines 25, as shown in FIGS. 7A, 7B and 7C. Each spine 25 is covered by a respective multi-lumened tubing 80 having, for example, a first lumen 81 through which the spine extends, a second lumen 82 for lead wires 40S, and a third lumen 83 for passing irrigation fluid via a passage 88 formed in the sidewall of the tubing 80 to annular space gap G between outer wall of the tubing 80 and side wall of the ring electrode 371 which are formed with fluid ports 85.

In some embodiments, the ring electrodes (irrigated or nonirrigated) are carried on the distal spine portions 25D. The plurality of ring electrodes on each spine may range between about 4 and 11, preferably about 6 and 9, and more preferably about 8. Depending on the plurality of spines, the distal electrode array 15 may carry a plurality of electrodes ranging between about 20 and 44, preferably between about 28 and 36 electrodes, and more preferably about 32 electrodes. In some embodiments, the electrode density is about 15 electrodes per square centimeter and dimensions of about 12 mm×18 mm.

In some embodiments, the spine supports 23 and the stem 46 are made of a material having shape-memory, i.e., that can be temporarily straightened or bent out of its original shape upon exertion of a force and is capable of substantially returning to its original shape in the absence or removal of the force. One suitable material for the support member is a nickel/titanium alloy. Such alloys typically comprise about 55% nickel and 45% titanium, but may comprise from about 54% to about 57% nickel with the balance being titanium. A nickel/titanium alloy is nitinol, which has excellent shape memory, together with ductility, strength, corrosion resistance, electrical resistivity and temperature stability. The spine supports may be formed from a sheet material which is, for example, die cut or laser cut into the configuration of the base and the spines. Side edges of the bases 23 may be affixed to inner surface of the stem 46 by any suitable manner, e.g., laser welding, adhesives, or the like. The non-conductive coverings 64 or the tubings 80 surrounding the spines 25 can be made of any suitable material, and is preferably made of a biocompatible plastic such as polyurethane or PEBAX.

At the junction of distal electrode array 15 and the stem 46, the non-conductive covering 64 or the multi-lumened tubing 80 of each spine 25 may be attached and sealed at its proximal end to the stem 46 by the polyurethane or the like.

The proximal ends of the lead wires 40S, 40D and 40P for the spine loop ring electrodes 37, and for the distal and proximal ring electrodes 38D and 38P proximal of the array 15, respectively, are electrically connected to a suitable connector (not shown) in the distal end of the control handle 16, which is connected to a source of ablation energy, e.g., RF energy, as is known in the art. The lead wires 40S, 40D and 40P extend through the central lumen 18 of the catheter body 12 (FIG. 2B). The lead wires 40S extend through the first lumen 31 of the tubing 19 of the intermediate section 14, and the lead wires 40D and 40P extend through the third lumen 33 of the tubing 19 (FIGS. 2C and 3C). Passing through the holes 58 in the washers 50D and 50P, the lead wires 40S extend through the polytube 68 which protects them from being damaged by the hole 58 (FIG. 3D).

In the depicted embodiment, the lead wires 40S extending through the central lumen 18 of the catheter body 12 and the first lumen 31 in the deflection section 14 may be enclosed within a protective sheath 94 to prevent contact with other components in the catheter. The protective sheath can be made of any suitable material, preferably polyimide. As would be recognized by one skilled in the art, the protective sheath can be eliminated if desired.

The ring electrodes 37, 37I and 38D and 38P are made of any suitable solid conductive material, such as platinum or gold, preferably a combination of platinum and iridium, and mounted onto the non-conductive cover 64 and the stem 46 with glue or the like. Alternatively, the ring electrodes can be formed by coating the non-conductive cover 64 and stem 46 with an electrically conducting material, like platinum, gold and/or iridium. The coating can be applied using sputtering, ion beam deposition or an equivalent technique.

In some embodiments, each ring electrode carried on the spines 25 is relatively short, having a length ranging from about 0.4 mm to about 0.75 mm. Moreover, the electrodes may be arranged in pairs, where two electrodes of a pair are spaced more closely to each other than they are to other pairs of electrodes. The closely-spaced electrode pairs allow for more accurate detection of near field pulmonary vein potential versus far field atrial signals, which is very useful when trying to treat atrial fibrillation. Specifically, the near field pulmonary vein potentials are very small signals whereas the atria, located very close to the pulmonary vein, provides much larger signals. Accordingly, even when the mapping array is placed in the region of a pulmonary vein, it can be difficult for the physician to determine whether the signal is a small, close potential (from the pulmonary vein) or a larger, farther potential (from the atria). Closely-spaced bipole electrodes permit the physician to more accurately determine whether he is looking at a close signal or a far signal. Accordingly, by having closely-spaced electrodes, one is able to target exactly the locations of myocardial tissue that have pulmonary vein potentials and therefore allows the clinician to deliver therapy to the specific tissue. Moreover, the closely-spaced electrodes allow the physician to determine the exact anatomical location of the ostium/ostia by the electrical signal.

In some embodiments, a proximal electromagnetic position sensor 42P is housed in the lumen 48 of the stem 46 (FIG. 4A). A sensor cable 36P extends from a proximal end of the position sensor 42P, and through the hole 57 of the washers 50 (FIG. 3D), the third lumen 33 of the tubing 19 of the deflection section 14 (FIG. 2C), and the central lumen 18 of the catheter body 12 (FIG. 2B). The cable 36P is attached to a PC board in the control handle 16, as known in the art. In some embodiments, one or more distal electromagnetic position sensors may be housed in the array, for example, in one or more distal portions of the array. Sensor cable(s) 36D may extend through the lumen 65 of spine covering 64 (FIG. 4B) or a fourth lumen 84 of the tubing 80 (FIG. 7C).

As shown in FIGS. 2A and 2C, the puller wires 24 and 26 (whether as two separate tensile members or parts of a single tensile member) are provided for bi-directional deflection of the intermediate section 14. The puller wires 24 and 26 are actuated by mechanisms in the control handle 16 that are responsive to a thumb control knob or a deflection control knob 11. Suitable control handles are disclosed in U.S. Pat. Nos. 6,123,699; 6,171,277; 6,183,435; 6,183,463; 6,198,974; 6,210,407 and 6,267,746, the entire disclosures of which are incorporated herein by reference.

The puller wires 24 and 26 extend through the central lumen 18 of the catheter body 12 (FIG. 2A) and through the second and fourth lumens 32 and 34, respectively, of the tubing 19 of the deflection section 14 (FIG. 2C). As shown in FIGS. 3A and 3C, they extend through holes 54 and 56, respectively of the washers 50. Where the puller wires are part of a single tensile member, the single tensile member has a U-bend 24/26U (FIG. 3A) at the distal face of the distal washer 50D which anchors the distal ends of the puller wires. In that regard, the U-bend extends through a short protective tubing 70 to protect the puller wires from the holes 54 and 56. Alternatively, where the puller wires are separate tensile members, their distal ends may be anchored via T-bars, as known in the art and described in, for example, U.S. Pat. No. 8,603,069, the entire content of which is incorporated herein by reference. In any case, the puller wires 24 and 26 are made of any suitable metal, such as stainless steel or Nitinol, and each is preferably coated with TEFLON or the like. The coating imparts lubricity to the puller wires. The puller wires preferably have a diameter ranging from about 0.006 to about 0.010 inch.

A compression coil 66 is situated within the central lumen 18 of the catheter body 12 in surrounding relation to each puller wire 24, as shown in FIG. 2B. Each compression coil 66 extends from the proximal end of the catheter body 12 to the proximal end of the intermediate section 14. The compression coils 66 are made of any suitable metal, preferably stainless steel. Each compression coil 66 is tightly wound on itself to provide flexibility, i.e., bending, but to resist compression. The inner diameter of the compression coil 66 is preferably slightly larger than the diameter of its puller wire.

The Teflon coating on each puller wire allows it to slide freely within its compression coil.

The compression coil 66 is anchored at its proximal end to the outer wall 20 of the catheter body 12 by a proximal glue joint (not shown) and at its distal end to the intermediate section 14 by a distal glue joint 92. Both glue joints may comprise polyurethane glue or the like. The glue may be applied by means of a syringe or the like through a hole made the sidewalls of the catheter body 12 and the tubing 19. Such a hole may be formed, for example, by a needle or the like that punctures the sidewalls which are heated sufficiently to form a permanent hole. The glue is then introduced through the hole to the outer surface of the compression coil 66 and wicks around the outer circumference to form a glue joint about the entire circumference of the compression coil.

Within the second and fourth lumens 32 and 34 of the intermediate deflection section 14, each puller wire 24 and 26 extends through a plastic, preferably Teflon, puller wire sheath 39 (FIGS. 2A and 2C), which prevents the puller wires from cutting into the wall of the tubing 19 of the deflection section 14 when the deflection section 14 is deflected.

In some embodiments, the ring electrodes 38D and 38P proximal of the array 15 serve as reference electrodes for visualization of the catheter on a 3-D mapping system, such as CARTO.RTM 3 SYSTEM available from Biosense Webster, Inc., which automatically locates the EM sensor 42, processes reference location values from electrodes 38D and 38P, which are at a constant location from the EM sensor(s) and determines the location of the electrodes 37 and 371 and visualizes the remainder of the electrode array 15.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Also, different features of different embodiments may be combined as needed or appropriate. Moreover, the catheters described herein may be configured to apply various energy forms, including microwave, laser, RF and/or cryogens. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter, comprising:
    an elongated catheter body; and
    an electrode array distal of the catheter body, the array comprising:
        a first spine support including a first base disposed in a first plane;
        a second spine support including a second base disposed in a second plane offset from the first plane;
        a first spine extending from the first base;
        a second spine extending from the second base;
        a first non-conductive covering disposed about the first spine, the first non-conductive covering including a first outer wall and a first passage disposed through the first outer wall; and
        a first ring electrode mounted over the first passage and defining a first gap between the first outer wall and a side wall of the first ring electrode.

2. The catheter of claim 1, in which the first ring electrode comprises a set of fluid ports.

3. The catheter of claim 2, in which the first non-conductive covering comprises a first lumen through which the first spine extends and a second lumen for passing irrigation fluid to the gap through the first passage.

4. The catheter of claim 3, further comprising a second non-conductive covering disposed about the second spine, the second non-conductive covering including a second outer wall and a second passage disposed through the second outer wall.

5. The catheter of claim 4, in which a second ring electrode is mounted over the second passage and defines a second gap between the second outer wall and a side wall of the second ring electrode.

6. The catheter of claim 3, in which the first non-conductive covering comprises a third lumen.

7. The catheter of claim 6, in which a first set of lead wires are disposed in the third lumen and connected to the first ring electrode.

8. The catheter of claim 7, in which the first set of lead wires extends through the elongated catheter body toward the distal array.

9. The catheter of claim 8, in which a distal portion of the first set of lead wires diverges from a distal portion of a second set of lead wires such that the distal portion of the first set of lead wires extends toward the first spine and a distal portion of the second set of lead wires extends toward the second spine.

10. The catheter array of claim 9, in which a proximal portion of the first set of lead wires and a proximal portion of the second set of lead wires are disposed in a single lumen of elongated catheter body.

11. The catheter array of claim 10, in which an intermediate portion of the first set of lead wires and an intermediate portion of the second set of lead wires are disposed in a single protective tube disposed in the elongated catheter body.

* * * * *